(12) United States Patent
Wyckoff et al.

(10) Patent No.: US 9,830,422 B1
(45) Date of Patent: Nov. 28, 2017

(54) IN SILICO BIOLOGICAL AND PHARMACEUTICAL MODELING

(71) Applicants: Gerald Wyckoff, Overland Park, KS (US); Scott Foy, Tucson, AZ (US)

(72) Inventors: Gerald Wyckoff, Overland Park, KS (US); Scott Foy, Tucson, AZ (US)

(73) Assignee: The Curators of the University of Missouri, Columbia, MO (US)

(*) Notice: Subject to any disclaimer, the term of this patent is extended or adjusted under 35 U.S.C. 154(b) by 691 days.

(21) Appl. No.: 14/337,751

(22) Filed: Jul. 22, 2014

Related U.S. Application Data

(60) Provisional application No. 61/958,174, filed on Jul. 22, 2013.

(51) Int. Cl.
  *G06F 19/12* (2011.01)
  *G06F 17/50* (2006.01)
  *G06N 7/00* (2006.01)

(52) U.S. Cl.
  CPC .............. *G06F 19/12* (2013.01); *G06F 17/50* (2013.01); *G06N 7/005* (2013.01)

(58) Field of Classification Search
  CPC ............................ G06F 17/5018; G06F 19/16
  USPC ........................................................ 703/2, 11
  See application file for complete search history.

(56) References Cited

U.S. PATENT DOCUMENTS

| | | | | |
|---|---|---|---|---|
| 5,884,230 | A | * | 3/1999 | Srinivasan ............... C07K 1/00 530/300 |
| 6,711,432 | B1 | * | 3/2004 | Krause .................... A61B 17/15 128/922 |
| 8,391,590 | B2 | * | 3/2013 | Yalla ....................... G06K 9/00 340/5.53 |
| 8,415,151 | B2 | * | 4/2013 | Wei ........................ C07K 14/56 435/351 |
| 2013/0253894 | A1 | * | 9/2013 | Honig ..................... G06F 19/12 703/11 |

* cited by examiner

*Primary Examiner* — Andy Ho
(74) *Attorney, Agent, or Firm* — Shook, Hardy & Bacon L.L.P.

(57) ABSTRACT

Systems, methods and computer-readable media are described herein for determining a protein's most-likely structural alignment. A maximum likelihood algorithm is utilized that compares possible input protein structural translocations with a template protein. It then calculates the optimally superimposed position for each input protein utilizing a distance-based probability scoring algorithm that accurately manages extreme distances.

20 Claims, 8 Drawing Sheets
(3 of 8 Drawing Sheet(s) Filed in Color)

IN SILICO BIOLOGICAL AND PHARMACEUTICAL MODELING

CROSS-REFERENCE TO RELATED APPLICATION

This application claims priority to U.S. Application No. 61/958,174, filed Jul. 22, 2013 and entitled "System and Method for In Silico Biological and Pharmaceutical Modeling." The entirety of the aforementioned application is incorporated by reference herein.

GRANT STATEMENT

None.

FIELD OF THE INVENTION

The present invention relates to computational modeling systems for biological and pharmaceutical experimentation and drug development.

BACKGROUND OF THE INVENTION

The bioactive properties of a protein are primarily a function of that protein's structure. Though research may focus on one particular application, a single protein may be reactive with many different proteins within the body. When such a protein is being developed as a potential drug, these other interactions can result in inefficiency due to blood plasma bonding, harmful side effects or even useful off-label uses.

Laboratory experiments for drug discovery traditionally required in vitro experimentation to study behavior between molecules and proteins in control test conditions, with the later possibility of in vivo experiments in animals. Computer-modeled experimentation, or "in silico" experimentation, has been shown to be a faster, cheaper and safer alternative to in vitro or in vivo experimentation.

To aid in silico research, the Protein Database (PDB) has been established and is freely accessible to researchers. PDB files give three-dimensional spatial coordinates for each atom in a given protein. Due to the breadth of the data base and the ease of access, the PDB file format is a widely accepted convention for in silico research.

Effective computer modeling requires highly accurate modeling of the structure of the individual proteins. The natural structure of a protein is determined by its chemical bond structure, called the primary structure, and the folded arrangement the protein occupies in three-dimensional space, called the secondary structure. The secondary structure of a protein is the arrangement which is generally the most compact possible, with the lowest energy state. Protein structures are generally composed of subunits, where each subunit has a characteristic structure and profile. Structure of the entire protein can be described as a composite of the individual subunits.

Existing superpositioning software is capable of atomic-level distance minimization of proteins to attempt to predict bonding structure, but the accuracy of this software is dependent on preliminary protein sequencing alignment. Because of its dependence on preliminary protein sequencing alignment, existing superpositioning software cannot be used for superimposing divergent homologous protein structures.

Existing structural alignment software is able to predict protein alignment without preliminary sequencing. But such software generally calculates distance minimization on the fold-level, by pairing a short list of oligopeptides which are known to have high affinity, rather than on the atomic-level, leading to bonding structure predictions which undermine the individual proteins' secondary structures. Further, because sequence alignment is based on matching oligopeptide pairs, it is not possible to obtain a complete sequence alignment of the protein. Additionally, because structural alignment software does not perform calculations on the atomic-level, existing structural alignment software is incapable of generating PDB format files.

Another method is to model atomic-level alignments and use statistical analysis to determine the most likely arrangement. Though computationally intensive due to the enormous numbers of possible configurations, calculating possible arrangements of atoms in a three-dimensional protein structure is not prohibitively difficult. The challenge is in determining the configurations which are most likely to be correct.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for predicting protein structure and bonding behavior. In exemplary aspects, a protein superimposing program is used to estimate the relative spatial coordinates for each atom in the protein by applying statistical analysis to possible three-dimensional (3D) arrangements of the protein. The output of this program gives the 3D coordinates for each atom in the same data format (e.g., the PBD file format) as experimentally determined protein structures, making them readily accessible as inputs to other in silico programs. Unlike existing structural alignment programs, the protein superimposing program described herein does not require a preliminary sequence alignment. Thus, the protein superimposing program described herein is capable of aligning distant homologs without a minimum sequence identity threshold.

The protein superimposing program of the current invention applies a maximum likelihood algorithm that superimposes proteins on an atomic level. Those alignments with probabilities below a predefined threshold may be eliminated from further consideration to reduce processor time. Because proteins are superimposed on an atomic level, the generated sequence alignment is derived from the entire protein structure and not merely the ologopeptide structural matches as with existing structural alignment programs. Further, superimposition at an atomic level helps to eliminate the often overweighed alignment contribution of secondary structures.

More specifically, the protein superimposing program described herein implements a maximum likelihood algorithm that compares possible input protein structural translocations with a template protein. It then calculates the optimally superimposed position for each input protein utilizing a distance-based probability scoring algorithm that accurately manages extreme distances.

BRIEF DESCRIPTION OF THE DRAWINGS

Embodiments are described in detail below with reference to the attached drawing figures. The patent or application file contains at least one drawing executed in color. Copies of this patent or patent application publication with color drawing(s) will be provided by the Office upon request and payment of the necessary fee.

DETAILED DESCRIPTION

Figure 1:
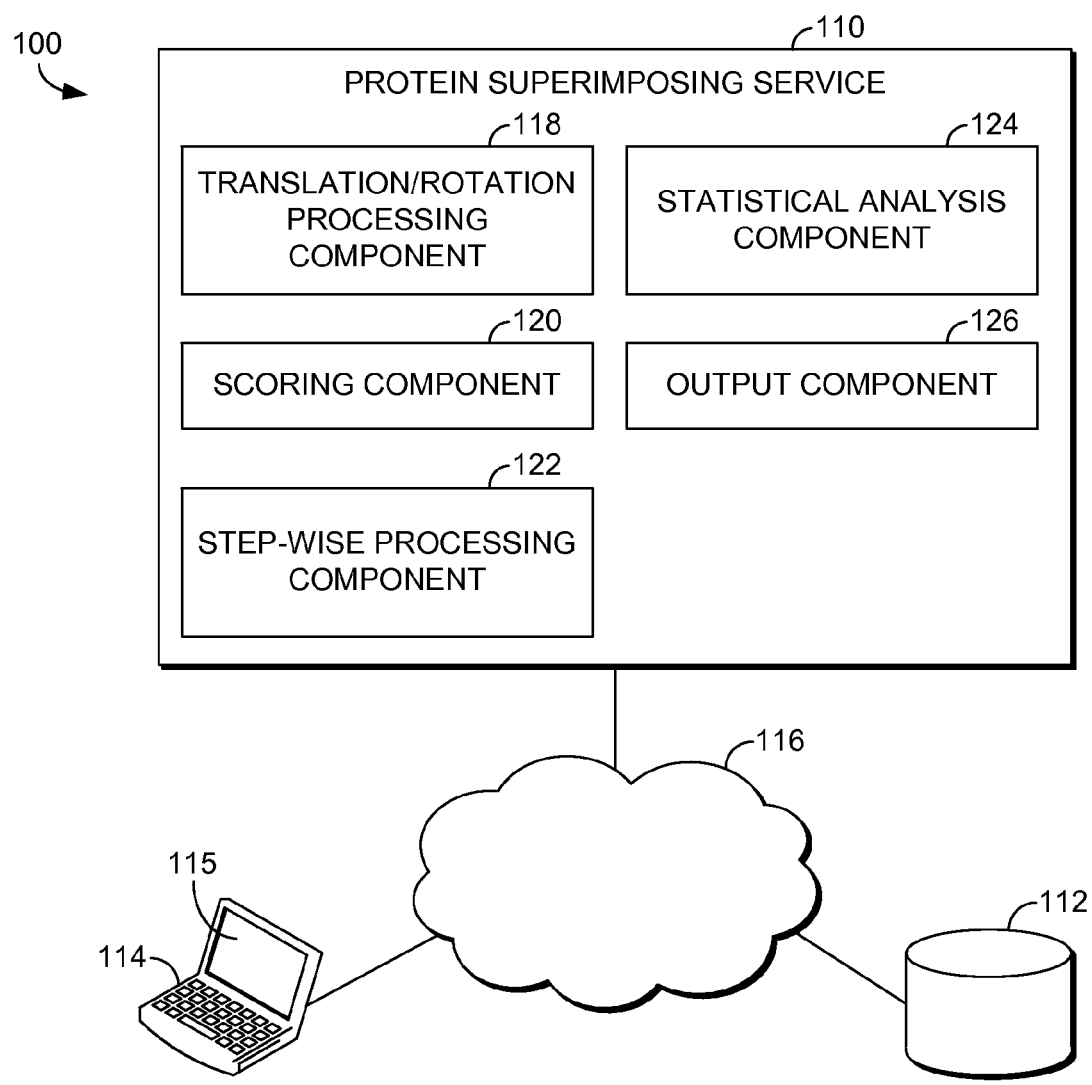
FIG. 1 is a block diagram of an exemplary computing system environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for utilizing a protein superimposing program that applies a maximum likelihood algorithm to evaluate the optimal alignment for a particular protein. Those alignments with probabilities below a predefined threshold may be eliminated from further consideration. The determination of optimal protein alignment may occur in a number of steps or phases. In Phase 1, a stationary template protein is selected based on the template protein being spatially larger than all other candidates. A range of mobile proteins is tested against this stationary template protein by rotating and translating each mobile protein relative to the template protein in a 3D coordinate space by a specified distance and angle. As the mobile protein moves, its position at any point in time is a pseudostate of the protein, where a pseudostate may be defined in terms of three defined transitional parameters and three defined rotational parameters, each measured relative to the spatial center of the protein, and a structural parameter representing the possible 3D structure of the protein. After testing, the resulting set of pseudostates is scored based on the standard deviation from the superimposed template protein. The top 25% scoring pseudostates is then retained and entered into the second phase.

In phase 2, variations of the surviving pseudostates are generated by adjusting each of the transitional and rotational coordinates, this time by half the prior defined interval. The lower-scoring pseudostates are eliminated, the interval halved again, and the phase 2 process is repeated until the interval is reduced to a predefined tolerance.

In phase 3, the pseudostate with the least mean center error distance (MCED) is selected as the new template protein. The remaining pseudostates are then tested against this new template protein, with their transitional and rotational parameters being limited as a function of their own MCED, such that the pseudostates converge towards the lowest MCED. The pseudostate achieving the highest statistical likelihood of superposition is then retained as the final structural alignment.

As a preface to the more detailed discussion below, discussion will be provided regarding protein geometry terminology and use of the maximum likelihood algorithm. When represented as a Protein Databank (PDB) file, a protein is a static structure whose atoms are points in a three-dimensional space. This space possesses x-, y-, and z-axes to enable the PDB file to display atoms in terms of x-, y-, and z-coordinates. Using the coordinates of every atom in a protein, the greatest x-coordinate ($x_{max}$) and the least x-coordinate ($x_{min}$) indicate the protein's x-axis' spatial perimeter. The distance (in angstroms) between $x_{min}$ and $x_{max}$ is the x-axis diameter ($\delta_x$). These same definitions of spatial perimeter and diameter also apply to the y- and z-axes (i.e., $\delta_y$ and $\delta_z$). Together, the spatial perimeters of all three axes comprise the protein's total spatial perimeter.

The spatial center ($c_A$) of a protein, which is the center of the protein based upon the spatial perimeter, is defined as follows:

$$c_\Delta = (x_{max} - x_{min}, y_{max} - y_{min}, z_{max} - z_{min})$$

The mean center ($c_\mu$) of a protein is the average of all the atomic coordinates that compose the protein:

$$c_\mu = \left( \frac{\sum x_n}{n_{atoms}}, \frac{\sum y_n}{n_{atoms}}, \frac{\sum z_n}{n_{atoms}} \right)$$

where $n_{atoms}$ is the total number of atoms in the protein.

The maximum likelihood (ML) algorithm is used to ascertain the most probable solution for a problem. In its most generic format, the ML algorithm calculates every possible solution to a problem. The probability or likelihood ($\pounds$) of each possible solution (i.e., a pseudostate in the case of the present invention) is then measured relative to the ideal solution (i.e., the template protein in the case of the present invention). Consequently, the solution most similar to that of the ideal (i.e., the one with the greatest $\pounds$; denoted max($\pounds$)) is selected as the most likely solution to the problem.

Given a pseudostate, $\pounds$ of the pseudostate will change as the value of one of its parameters changes. Geometrically, a x-axis represents the range of the changing parameter and a y-axis represents $\pounds$. The parameter value that generates max($\pounds$) can be calculated by setting the derivative of the curve equal to zero (the derivative-based approach). Alternatively, calculating $\pounds$ at specific intervals of the parameter (the brute-force approach) will also generate the likelihood curve. Note that increasing or decreasing the parameter value by the interval generates a new pseudostate. Furthermore, decreasing the interval size increases the number of possible pseudostates to be generated. A new axis is added to the geometric system for each changing parameter. Therefore, the brute-force approach implies that increasing the number of changing parameters increases the number of possible pseudostates.

Turning now to FIG. 1, an exemplary computing system environment 100 is depicted suitable for use in implementing embodiments of the present invention. The computing system environment 100 is merely an example of one suitable computing system environment and is not intended to suggest any limitation as to the scope of use or functionality of embodiments of the present invention. Neither should the computing system environment 100 be interpreted as having any dependency or requirement related to any single module/component or combination of modules/components illustrated therein.

The computing system environment 100 includes a protein superimposing service 110, a data store 112, and an end-user computing device 114 all in communication with one another via a network 116. The network 116 may include, without limitation, one or more local area networks (LANs) or wide area networks (WANs). Such networks are commonplace and, as such, no further description is provided.

In some embodiments, one or more of the illustrated components/modules may be implemented as stand-alone applications. In other embodiments, one or more of the illustrated components/modules may be integrated directly into the operating system of the protein superimposing service 110. The components/modules illustrated in FIG. 1 are exemplary in nature and in number and should not be construed as limiting. Any number of components/modules may be employed to achieve the desired functionality within the scope of embodiments hereof. Further, components/modules may be located on any number of servers. By way of example only, the protein superimposing service 110 might reside on a server, a cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 112 is configured to store information for use by, for example, the protein superimposing service 110 and/or the end-user computing device 114. The information stored in association with the data store 112 is configured to be searchable for one or more items of information stored in association therewith. The information stored in association with the data store 112 may comprise general information used by the protein superimposing service 110 and/or the end-user computing device 114. For example, the data store 112 may store a catalog of proteins to be analyzed by the protein superimposing service 110. Further, the data store 112 may store results or outputs generated by the protein superimposing service 110 such as output files containing spatial coordinates of the analyzed proteins.

The content and volume of such information in the data store 112 are not intended to limit the scope of embodiments of the present invention in any way. Further, though illustrated as a single, independent component, the data store 112 may, in fact, be a plurality of storage devices, for instance, a database cluster, portions of which may reside on the protein superimposing service 110, the end-user computing device 114, and/or any combination thereof.

As shown, the end-user computing device 114 includes a display screen 115. The display screen 115 is configured to display information to the user of the end-user computing device 114, for instance, information relevant to communications initiated by and/or received by the end-user computing device 114. Embodiments are not intended to be limited to visual display but rather may also include audio presentation, combined audio/visual presentation, and the like. The end-user computing device 114 may be any type of computing device such as a computer, tablet PCs, PDAs, mobile phones, and/or smart phones. Interaction with the computing device 114 may be via a touch pad, a pointing device, and/or gestures.

Components of the protein superimposing service 110 may include a processing unit, internal system memory, and a suitable system bus for coupling various system components, including one or more data stores for storing information (e.g., files and metadata associated therewith). The protein superimposing service 110 typically includes, or has access to, a variety of computer-readable media.

The computing system environment 100 is merely exemplary. While the protein superimposing service 110 is illustrated as a single unit, it will be appreciated that the protein superimposing service 110 is scalable. For example, the protein superimposing service 110 may in actuality include a plurality of computing devices in communication with one another. Moreover, the data store 112, or portions thereof, may be included within, for instance, the protein superimposing service 110 as a computer-storage medium. The single unit depictions are meant for clarity, not to limit the scope of embodiments in any form.

As shown in FIG. 1, the protein superimposing service 110 comprises a translation/rotation processing component 118, a scoring component 120, a step-wise processing component 122, a statistical analysis component 124, and an output component 126. In some embodiments, one or more of the components 118, 120, 122, 124, and 126 may be implemented as stand-alone applications. In other embodiments, one or more of the components 118, 120, 122, 124, and 126 may be integrated directly into the operating system of a computing device such as the computing device 114 of FIG. 1. It will be understood that the components 118, 120, 122, 124, and 126 illustrated in FIG. 1 are exemplary in nature and in number and should not be construed as limiting. Any number of components may be employed to achieve the desired functionality within the scope of embodiments hereof.

The translation/rotation processing component 118 may be utilized in Phase 1 of the protein superimposing program and is configured to identify translational, rotational, and structural alignment pseudostates, $S_n$, of a mobile protein, $P_m$, relative to a stationary template protein, $P_t$. To limit the number of possible pseudostates to a finite number, $S_n$, the translation/rotation processing component 118 utilizes a bounded translation and rotation model where translation of the $P_m$ is bounded by a specified distance, and rotation of the $P_m$ is bounded by a specified angle. More specifically, the translation length between $S_n$ and $S_{n+1}$ is $L_0$, while the rotation angle between $S_n$ and $S_{n+1}$ is $\theta_0$. $P_m$ perpendicularly translates by $L_0$ in the direction of each three-dimensional axis (in both positive and negative directions). That is, $P_m$ does not translate diagonally relative to the three axes. A new pseudostate is generated for each $L_0$. Additionally, $P_m$ rotates unidirectionally by $\theta_0$ around each of the three axes. Within the translation boundary, for each pseudostate that is translated by $L_0$, $P_m$ will be rotated by $\theta_0$ multiple times along each axis until $P_m$ has been rotated by one radian around each axis. A new pseudostate is generated for each $\theta_0$ around any axis. Despite a rotation of only one radian per axis, $P_m$ can still invert completely due to cumulative rotation along all three axes.

As $P_m$ translates by $L_0$, it is restrained within a boundary around $P_t$. The translation boundary for Phase 1 is the spatial perimeter of $P_t$. The spatial center, $c_A$, of $P_m$ is prohibited from exiting the cube generated by this spatial perimeter. During Phases 1 and 2, $P_t$ is selected to be the largest input protein (based on cubic angstroms using the spatial perimeter dimensions) to establish the correct boundary. If $P_m$ was the larger protein, it is possible that $P_t$ would never superimpose the periphery of $P_m$.

The scoring component 120 may also be used in Phase 1 of the protein superimposing program and is configured to generate probabilities of superimposition for each of the pseudostates and identify those pseudostates having probabilities above a predefined threshold. The probability or likelihood, $\mathcal{L}$, of a pseudostate is measured relative to $P_t$. To determine the probability of superimposing two atoms (one from the $P_m$ and one from the $P_t$), the scoring component 120 utilizes a Gaussian probability curve as shown in FIG. 2.

Figure 2:
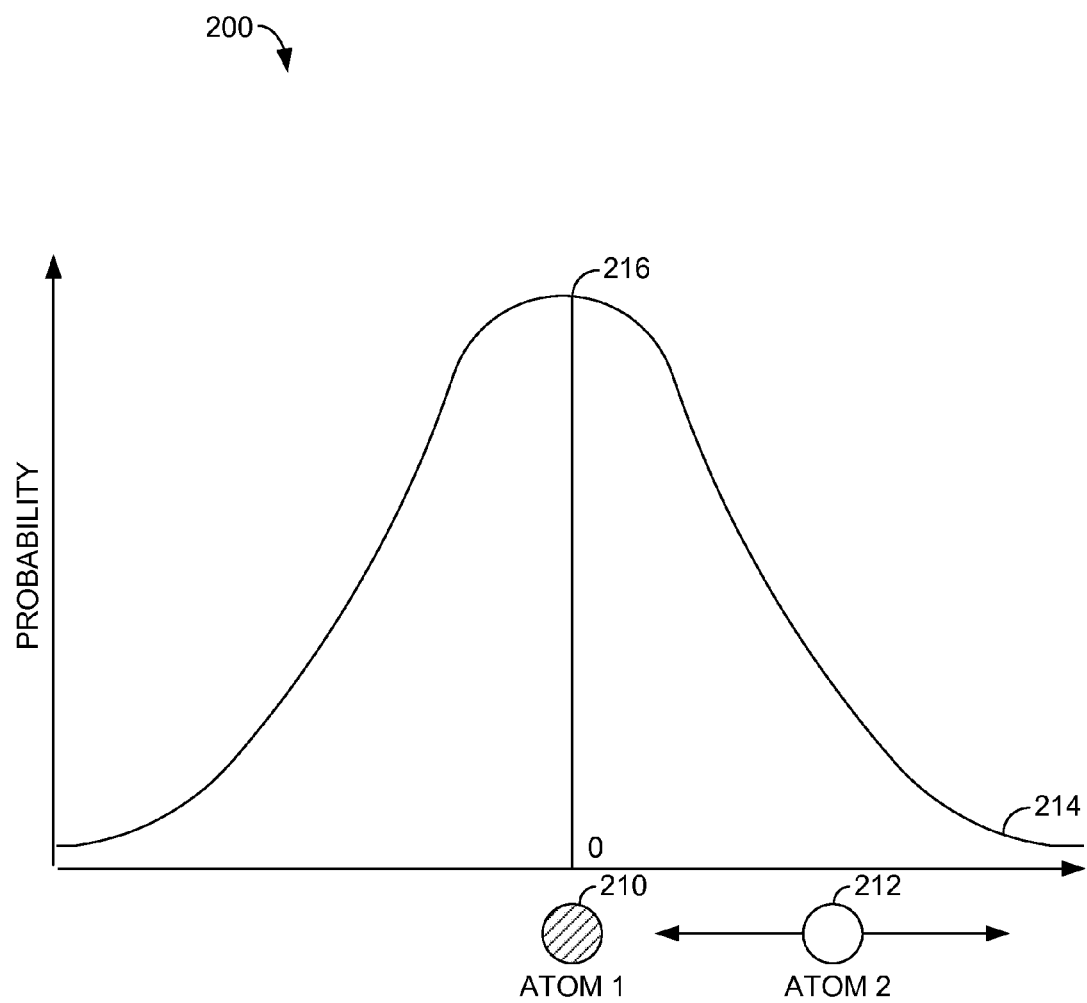
FIG. 2 is an exemplary Gaussian probability curve in accordance with an embodiment of the present invention.

The curve in FIG. 2, referenced generally by the numeral 200, illustrates that as the distance between the $P_t$ atom (atom 210) and the $P_m$ atom (atom 212) increases, the probability of superimposition decreases by approaching zero as shown by the reference numeral 214. Conversely, as the distance between atom 210 and atom 212 decreases, the probability of superimposition increases by approaching the zenith of the curve as shown by the reference numeral 216. This probability scoring measurement eliminates overweighing large atomic distances because the rate of change in the probability decreases as the probability curve 200 approaches the asymptote at the x-axis (as indicated generally by the reference numeral 214). Furthermore, when two atoms are close together, the probability scoring measurement will not emphasize moving them closer together at the expense of other atoms because of the plateau at the height of the probability curve 200 (as indicated generally by the reference numeral 212).

Based upon a normal probability distribution curve, the general formula for the probability (p) of a random point being at x location along the x-axis is as follows:

$$p = \left(\frac{1}{\sigma\sqrt{2\pi}}\right)e^{\frac{-(x-\mu)^2}{2\sigma^2}}$$

where $\sigma$ is the standard deviation and $\mu$ is the mean location of the points. However, when calculating the probability of two atoms superimposing, the mean ($\mu$) is equal to zero and x becomes the distance between the two atoms (d), thus simplifying the equation to:

$$p = \left(\frac{1}{\sigma\sqrt{2\pi}}\right)e^{\frac{-d^2}{2\sigma^2}}$$

The $\sigma$ is a measure of the deviation between the diameters ($\delta$) of all the proteins (to determine subunit homology) or subunits (to determine atomic probability). Importantly, $\sigma$ is averaged across all three dimensions, thus allowing a protein to rotate without having to recalculate $\sigma$ for each dimension. The protein standard deviation ($\sigma_p$) is calculated using the mean of all diameters ($\delta_\mu$) of the program's input proteins. That is, $\delta_\mu$ is the mean of the x-, y-, and z-axis diameters for every protein in the alignment:

$$\sigma_p = \sqrt{\frac{\sum(\delta - \delta_\mu)^2}{n_t - 1}}$$

The subunit standard deviation ($\sigma_s$) is calculated using the mean diameters from all the subunits of all input proteins. The mean diameter of a single subunit ($\delta_s$) in an input protein is calculated using the following equation:

$$\delta_s = \left(\frac{\delta_x \cdot \delta_y \cdot \delta_z}{n_s}\right)^{\frac{1}{3}}$$

where $n_s$ is the number of subunits in the protein and $\delta_{x/y/z}$ are the diameters for the subunit's respective protein. The mean diameter for all the subunits is then calculated by averaging $\delta_s$ for all the input proteins. The $\sigma_s$ calculation is finished using a population standard deviation equation:

$$\sigma_s = \sqrt{\frac{\sum(\delta_s - \delta_\mu)^2}{n_t}}$$

where $n_t$ is the total number of subunits in all the input proteins and $\delta_\mu$ is the mean diameter of all the subunits of all input proteins. Note that $\delta_s$ represents each subunit, not each protein; therefore, the same $\delta_s$ will be used multiple times if the protein possesses multiple subunits. Further note that when calculating $\sigma_p$, $\delta_\mu$ is the average of all the protein diameters, while $\delta_\mu$ is the average of all the subunit diameters when calculating $\sigma_s$.

Importantly, no degrees of freedom are subtracted when calculating $\sigma_s$ because every atom in the subunit is used in the $\sigma_s$ application (to determine atom probability). Conversely, $\sigma_p$ is a sample standard deviation equation that requires the subtraction of a degree of freedom. The sample standard deviation equation is used because its application (to determine subunit homology) uses only five amino acids per subunit (discussed subsequently), thus $\sigma_p$ represents only a sample of the total population of atoms.

Although the aforementioned equations calculate the probability of superimposing two homologous atoms, the scoring component 120 calculates $\mathcal{L}$ of superimposing entire protein structures for each pseudostate. First, the probability of each homologous pair of backbone atoms (alpha carbon, carboxyl carbon, and amine nitrogen) is calculated. To derive $\mathcal{L}$ of superimposing proteins in a pseudostate, the scoring component 120 multiplies the individual atomic probabilities ($p_{atom}$):

$$\mathcal{L}(I|S) = \Pi p_{atom}$$

where the function $\mathcal{L}(I|S)$ is the likelihood of the input parameters (I) given a pseudostate (S). This multiplication is a logical "and" statement, representing the probability of superimposing all homologous atoms. The input parameter (I) is the sequence arrangement that dictates homologous atoms. Additionally, the scoring component 120 delineates the pseudostate location (S) using three translation and three rotation parameters.

The scoring component 120 uses a combinatorics (i.e., an all-possible-combinations) algorithm to determine sequence homology. Duplicate amino acid matches are permitted and the sequence homology that generates max($£$) is the correct matching arrangement. Theoretically however, the number of possible sequence arrangements is too numerous to practically calculate $£$ for each arrangement. Therefore, the scoring component 120 performs heuristic steps to minimize the number of sequence arrangements to be calculated. Without these heuristic steps, calculating max($£$) would require calculating the probability between each amino acid from one protein to every amino acid in the second protein. However, the scoring component 120 predicts a limited range of amino acids from the $P_m$ to match each amino acid from the $P_t$. This range is determined by first calculating the difference between the two sequence lengths ($\Delta l$; will be at least ten percent of the longer sequence). Then, each amino acid in both sequences is converted from a position in the sequence to a percentage of the sequence (the n-terminus is zero percent and the c-terminus is one hundred percent). For each amino acid in the first sequence, an amino acid from the second sequence is selected that possesses approximately the same sequence percentage. The range for the second sequence is $\pm \Delta l$ from the selected amino acid. Generating this range operates on the assumption that a large deletion from one terminus and a correspondingly large insertion on the other terminus did not occur as the two sequences evolved independently.

To structurally align proteins composed of multiple subunits, the scoring component 120 first determines subunit homology of the input proteins. Subunit homology is determined by calculating which amino acids are 0, 25, 50, 75, and 100 percent of the sequence (initiated at the n-terminus) for each subunit for all the input proteins. The scoring component 120 makes the assumption that each subunit is composed of only these five amino acids; therefore, when calculating subunit probabilities, it will match only amino acids with the same sequence percentage. These individual atomic probabilities are then multiplied to obtain the probability of one subunit superimposing the other. Having only five amino acids per subunit makes performing an all-possible-combinations (of subunits) algorithm practical. The likelihood of each subunit combination is calculated by multiplying the individual subunit probabilities to obtain the total likelihood of superimposing the proteins. Importantly, when determining subunit homology, because the scoring component 120 calculates these probabilities utilizing only five amino acids per subunit, they are not the true probabilities of superimposing two subunits or proteins. Furthermore, because subunits can statistically deviate on a protein-scale, the probability calculations require that $\sigma_p$ be implemented as $\sigma$.

Because of the translation and rotation boundaries imposed by the translation/rotation processing component 118 and because of the numerous translation and rotations executed by the translation/rotation processing component 118, many pseudostates in $S_t$ produce mobile protein positioning that is either too distant or too transposed from the template protein to result in a meaningful $£$ (I|$S_n$). Therefore, the scoring component 120 utilizes a filtering algorithm to prevent the unnecessary lengthy probability calculation of significantly incorrect pseudostates. Calculating the complete $£$ requires the probability computation of every amino acid; therefore, the filtering algorithm uses the probability calculated when determining subunit homology because this calculation requires probability computation of only five amino acids per subunit. Once this probability is calculated for each $S_n$, the filtering algorithm will discard a certain percentage of the least probable pseudostates in $S_t$.

When calculating the percentage of $S_t$ to be removed by the filtering algorithm, the scoring component 120 assumes $P_t$ is a globular protein with an ellipsoid shape. Furthermore, the scoring component 120 assumes that any $S_n$ featuring the $c_\Delta$ of $P_m$ outside the general ellipsoid shape of $P_t$ but remaining within the spatial perimeter is likely to possess an unsatisfactory homologous subunit probability. Therefore, the percentage of $S_t$ to be filtered ($S_{\%}$) is expressed by the following equation:

$$S_\% = 1 - \frac{V_e}{V_c}$$

where $V_c$ is the cubic volume of the spatial perimeter and $V_e$ is the volume of the ellipsoid:

$$V_e = \frac{4}{3} \cdot \pi \cdot \frac{\delta_x}{2} \cdot \frac{\delta_y}{2} \cdot \frac{\delta_z}{2} = \frac{\pi \delta_x \delta_y \delta_z}{6}$$

Note that $\delta$ is the diameter and must be halved to equal the radius. Using the above $V_e$ equation, $S_\%$ equals the following value:

$$S_\% = 1 - \frac{\left(\frac{\pi \delta_x \delta_y \delta_z}{6}\right)}{\delta_x \delta_y \delta_z} = 1 - \frac{\pi}{6} \cong 0.48$$

Additionally, considering computational efficiency, the scoring component 120 assumes that half of the $S_n$ featuring the $c_\Delta$ of $P_m$ inside the general ellipsoid shape of $P_t$ will also possess unsatisfactory probabilities. Therefore, the scoring component 120 increases the calculated percentage of $S_t$ to be removed by the filtering algorithm to 75 percent.

Because $P_m$ translates within the voluminous spatial perimeter of $P_t$, the initial parameters of $L_0$ and $\theta_0$ are defined to be generously large to minimize the number of pseudostates in $S_t$. Although large initial parameters reduce the size of $S_t$, they may also decrease the accuracy of the structural alignment. To counteract this potential problem, the step-wise processing component 122 (utilized in Phase 2 of the protein superimposing program) gradually decreases the translation length of $L_0$ and the rotation angle of $\theta_0$ until they are less than or equal to a final pair of parameters containing lesser quantities ($L_f$ and $\theta_f$). Decreasing the sizes of the two initial parameters to those of the final parameters will increase the accuracy of the structural alignment without exponentially increasing $S_t$.

Thus, the step-wise processing component 122 receives the $S_t$ from the scoring component 120 and retains thirty-three percent of the pseudostates with the greatest $£$. The quantities of $L_0$ and $\theta_0$ are then halved ($L_{0.5}$ and $\theta_{0.5}$) and used to generate new pseudostates. A portion of these new pseudostates is generated by translating the retained pseudostates in $S_t$ by $L_{0.5}$ in the positive and negative direction of each axis. That is, each $S_n$ is translated by $L_{0.5}$ in each of the six directions (positive x-direction, negative x-direction, etc.) to generate six new pseudostates. The final portion of the new pseudostates is generated by rotating each $S_n$ (including those recently generated by a translation of $L_{0.5}$) along each axis in both the positive and negative directions by $\theta_{0.5}$. Once these new pseudostates are assembled into $S_t$, the step-wise processing component 122 calculates £ for each $S_n$ as outlined above. The step-wise processing component 122 then retains a specific number of those pseudostates in $S_t$ possessing the greatest £. In order to prevent the exponential growth of $S_t$, the number (not the percentage) of retained pseudostates is set to equal the number of pseudostates retained by the step-wise processing component 122; this number remains constant for all iterations. The parameters of $L_{0.5}$ and $\theta_{0.5}$ are then halved and the process repeats for multiple iterations until $L \le L_f$ and $\theta \le \theta_f$. For each $P_m$, the $S_n$ with the greatest £ is retained for the next processing step.

The statistical analysis component 124 is utilized in Phase 3 of the protein superimposing program and is configured to select a new $P_t$ and align it to the remaining proteins using another series of pairwise alignments as described above. The mobile protein that possesses the least mean center error distance (MCED), which is the distance between the $c_\mu$ of each input protein and the of all the proteins combined, is selected as the new $P_t$. Designating $P_t$ as the protein with the least MCED minimizes the total translational and rotational movement required for all the $P_m$s to structurally align to $P_t$. Therefore, each $P_m$ is converging on a $P_t$ that possesses the most "average" spatial position.

For each pairwise alignment between $P_m$ and the newly designated $P_t$, the statistical analysis component 124 generates new pseudostates similarly to those generated in Phase 2 of the program. However, only a single iteration using $L_f$ and $\theta_f$ is performed instead of several iterations that half $L$ and $\theta$. Moreover, instead of $P_m$ translating and rotating each iteration by only a single quantity of $L$ and $\theta$, the statistical analysis component 124 translates and rotates each $P_m$ by multiple quantities of $L_f$ and $\theta_f$. The number of quantities $P_m$ can translate and rotate is equal to $L_f/\text{MCED}$ (rounded to the nearest integer). That is, the MCED determines the translational and rotational deviation from the current position of $P_m$ relative to the position $P_m$ must achieve for adequately superimposing $P_t$. Once translation and rotation is completed, the statistical analysis component 124 calculates $£(l|S_n)$ of the pseudostates generated by this process. For each $P_m$, the statistical analysis component 124 then selects the $S_n$ achieving $\max(£)$ to be the final position of $P_m$ in the structural alignment.

Figure 3:
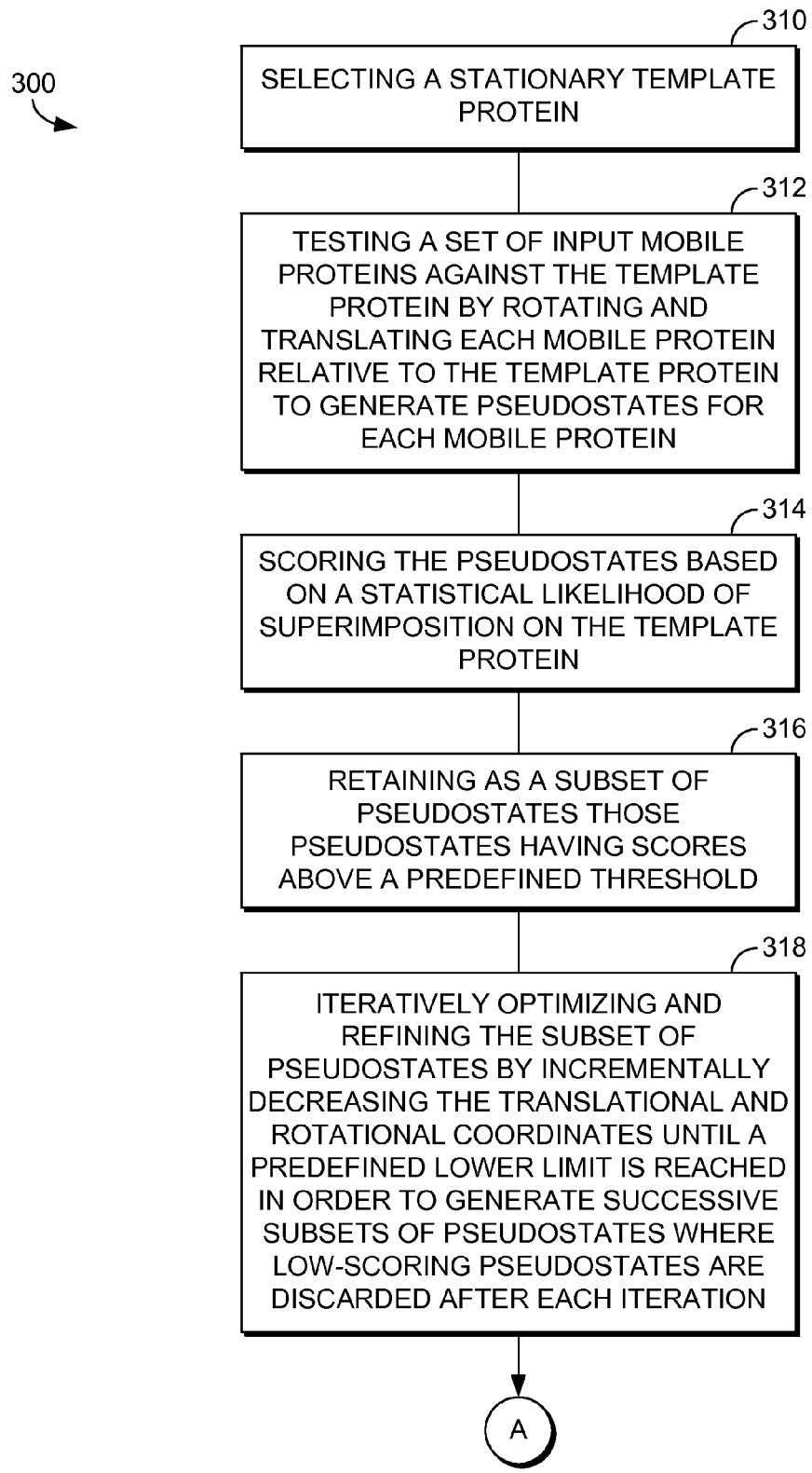
FIGS. 3-4 depict a flow diagram of an exemplary method of determining an input protein's most-likely structural alignment in accordance with an embodiment of the present invention.
Figure 4:
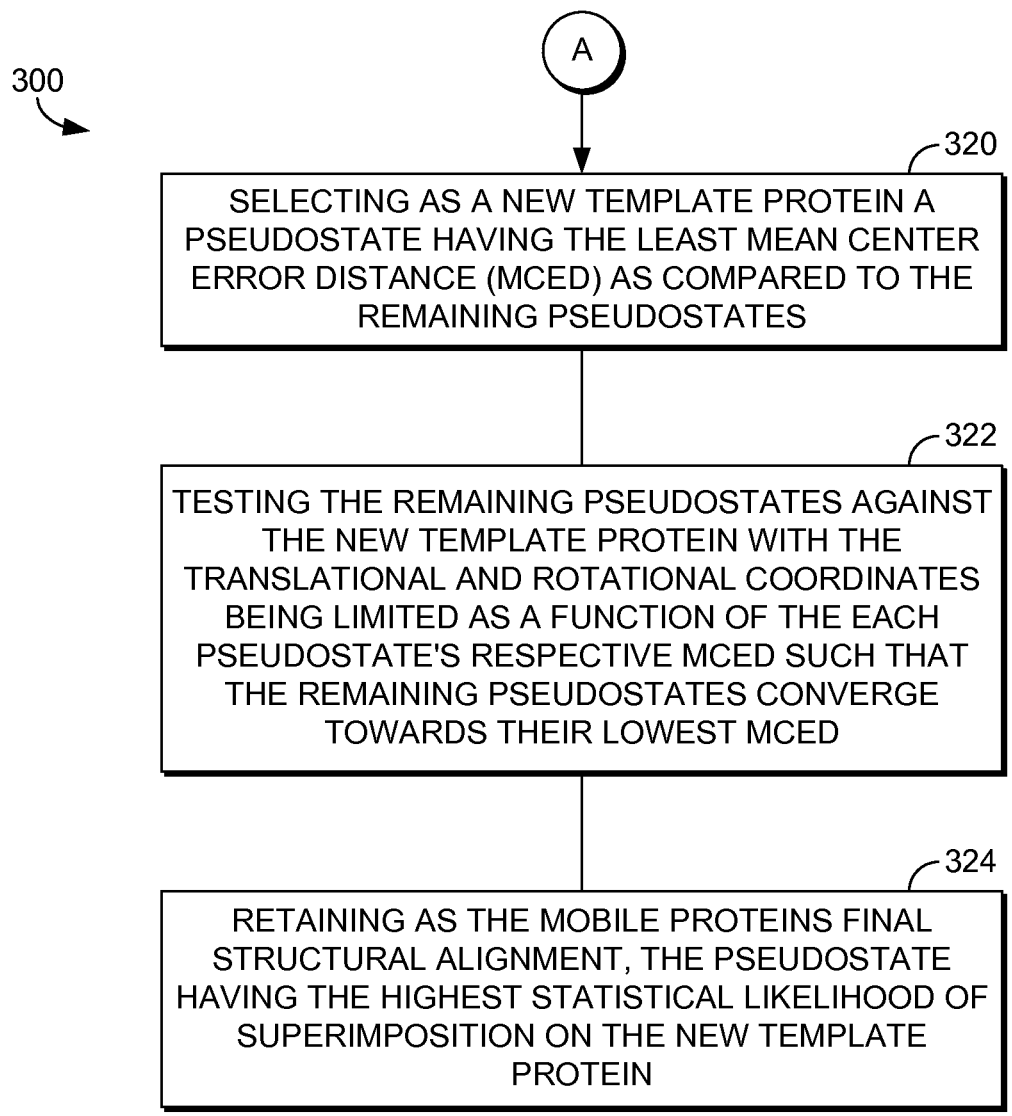

Turning now to FIGS. 3-4, the figures depict a flow diagram of an exemplary method 300 of determining an input protein's most-likely structural alignment. At a step 310, input proteins are received and one of the input proteins is selected to be a template protein. The largest input protein (i.e., the protein having the largest spatial perimeter dimensions as measured in cubic Angstroms) is selected to be the template protein. The template protein remains stationary within a 3D coordinate system (e.g., a coordinate system having x-, y-, and z-axes).

At a step 312, each of the input proteins is tested against the template protein. Testing occurs by rotating and translating each mobile protein relative to the template protein in the 3D coordinate system to generate pseudostates of the mobile protein. Translation occurs relative to each of the 3D axes in both a positive and negative direction by a fixed distance. As well, the translation bounds are limited to the spatial perimeter of the template protein. Continuing, rotation occurs unidirectionally around each of the 3D axes by a specified angle until the mobile protein has been rotated by one radian around each axis.

The pseudostates generated by the step 312 may be filtered using a filtering algorithm before proceeding to step 314. The filtering algorithm calculates a probability of superimposition on the template protein based on five amino acids per subunit basis versus on an atom-by-atom basis. A percentage of pseudostates having a low probability (e.g., a probability below a predefined threshold) of superimposition will be discarded. At step 314, the pseudostates remaining after the filtering algorithm has been executed are scored based on a statistical likelihood or probability of superimposing on the template protein. The probability calculation in this case is on an atomic or atom-by-atom basis.

At a step 316, the pseudostates scoring above a predefined threshold are retained for further processing. At a step 318, the pseudostates from step 316 are iteratively processed by incrementally decreasing the translational and rotational coordinates until a predefined lower limit is reached. For example, the translation and rotational coordinates may be incrementally halved until the predefined lower limit is reached for each. Each iteration produces a number of pseudostates, and each of the pseudostates is scored based on its statistical likelihood of superimposing, at the atomic level, on the template protein. A constant number of high-scoring pseudostates (e.g., pseudostates having a probability above a predefined threshold) is retained after each iteration for further processing.

The method 300 continues as shown in FIG. 4. At a step 320, a new template protein is selected from the pseudostates generated at step 318. The pseudostate having the least mean center error distance (MCED) as compared to the other pseudostates is selected as the new template protein. At a step 322, each of the remaining pseudostates generated at step 318 are tested against the new template protein by translating and rotating the pseudostates relative to the new template protein to generate a final set of pseudostates for each mobile protein. The translation length and the rotation angle are set to the predefined lower limit in step 318. Further, each pseudostate is rotated and translated multiple times. For instance, each pseudostate is rotated and translated by a number equal to the predefined lower limit for translation divided by the pseudostate's MCED (rounded to the nearest integer). By doing this, each of the remaining pseudostates converges towards its lowest MCED.

At a step 324, the pseudostate generated at step 322 that has the highest statistical likelihood (e.g., highest probability) of superimposing on the new template protein is retained as the mobile protein's final structural alignment. The method 300 may further comprise generating an output file describing the relative positions in the 3D coordinate system of the mobile protein's final structural alignment.

Exemplary Computing Environment

Figure 5:
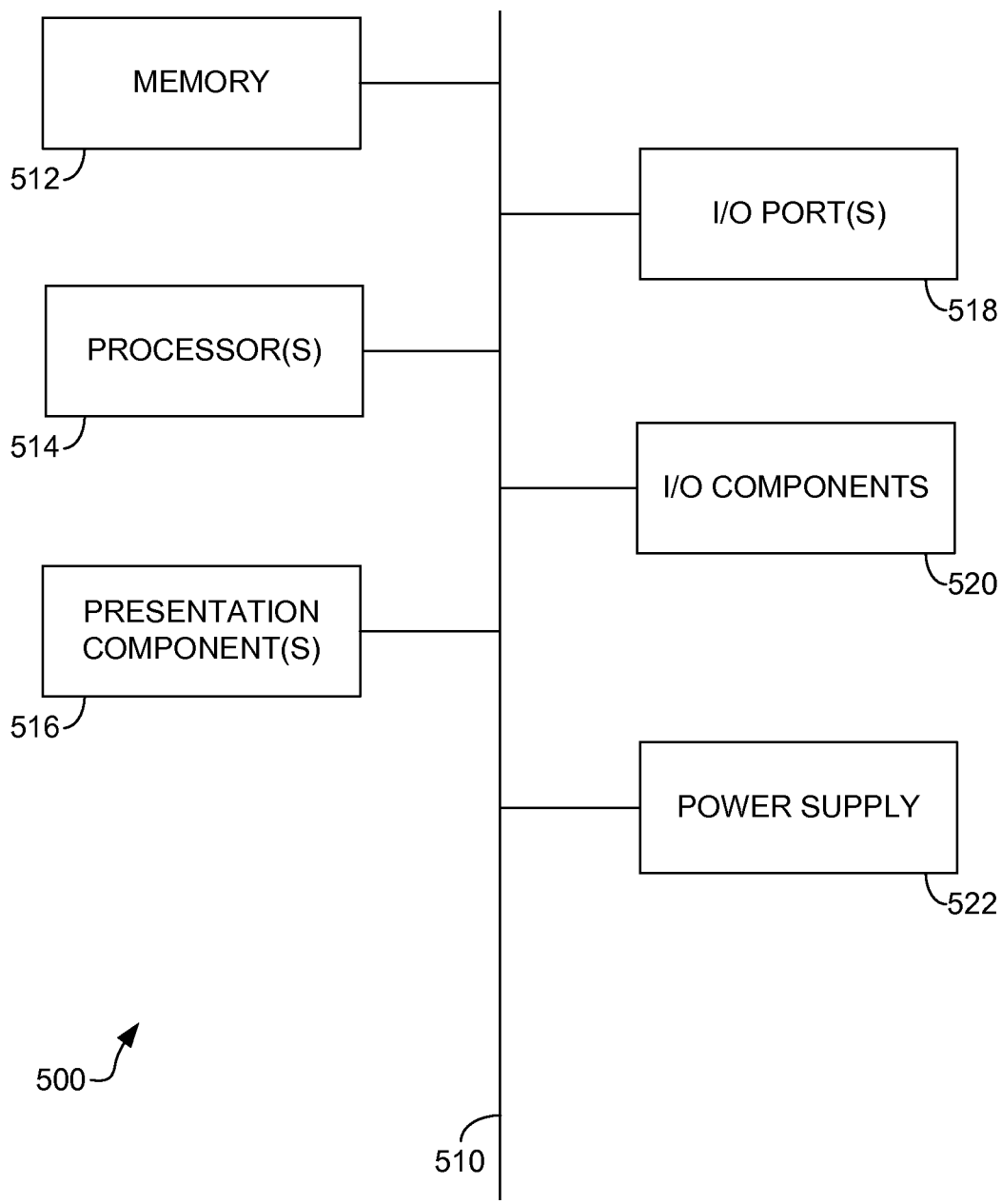
FIG. 5 depicts a block diagram of an exemplary computing environment suitable for use in implementing embodiments of the present invention.

FIG. 5 illustrates an exemplary operating environment in which embodiments of the present invention may be implemented is described below in order to provide a general context for various aspects of the present invention. Referring to the figures in general and initially to FIG. 5, in particular, an exemplary operating environment for implementing embodiments of the present invention is shown and designated generally as computing device 500. The computing device 500 is but one example of a suitable computing environment and is not intended to suggest any limitation as to the scope of use or functionality of embodiments of the invention. Neither should the computing device 500 be interpreted as having any dependency or requirement relating to any one or combination of components illustrated.

Embodiments of the invention may be described in the general context of computer code or machine-usable instructions, including computer-usable or computer-executable instructions such as program modules, being executed by a computer or other machine, such as a personal data assistant, a smart phone, a tablet PC, or other handheld device. Generally, program modules including routines, programs, objects, components, data structures, and the like, refer to code that performs particular tasks or implements particular abstract data types. Embodiments of the invention may be practiced in a variety of system configurations, including hand-held devices, consumer electronics, general-purpose computers, more specialty computing devices, etc. Embodiments of the invention may also be practiced in distributed computing environments where tasks are performed by remote-processing devices that are linked through a communications network. In a distributed computing environment, program modules may be located in both local and remote computer storage media including memory storage devices.

With continued reference to FIG. 5, the computing device 500 includes a bus 510 that directly or indirectly couples the following devices: a memory 512, one or more processors 514, one or more presentation components 516, one or more input/output (I/O) ports 518, one or more I/O components 520, and an illustrative power supply 522. The bus 510 represents what may be one or more busses (such as an address bus, data bus, or combination thereof). Although the various blocks of FIG. 5 are shown with lines for the sake of clarity, in reality, these blocks represent logical, not necessarily actual, components. For example, one may consider a presentation component, such as a display device, to be an I/O component. Also, processors have memory. The inventors hereof recognize that such is the nature of the art, and reiterate that the diagram of FIG. 5 is merely illustrative of an exemplary computing device that can be used in connection with one or more embodiments of the present invention. Distinction is not made between such categories as "workstation," "server," "laptop," "hand-held device," etc., as all are contemplated within the scope of FIG. 5 and reference to "computing device."

The computing device 500 typically includes a variety of computer-readable media. Computer-readable media may be any available media that is accessible by the computing device 500 and includes both volatile and nonvolatile media, and removable and non-removable media. Computer-readable media comprises computer storage media and communication media; computer storage media excludes signals per se. Computer storage media includes non-transitory volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 500. Communication media, on the other hand, embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The memory 512 includes computer-storage media in the form of any combination of volatile and nonvolatile memory. The memory may be removable, non-removable, or a combination thereof. Exemplary hardware devices include solid-state memory, hard drives, optical-disc drives, and the like. The computing device 500 includes one or more processors that read data from various entities such as the memory 512 or the I/O components 520. The presentation component(s) 516 present data indications to a user or other device. Exemplary presentation components include a display device, speaker, printing component, vibrating component, and the like.

The I/O ports 518 allow the computing device 100 to be logically coupled to other devices including the I/O components 520, some of which may be built in. Illustrative components include a microphone, joystick, game pad, satellite dish, scanner, printer, wireless device, and the like. Interaction with the I/O components 520 may be via voice, touch, gestures, keyboard, a pointing device such as a mouse, and the like.

Furthermore, although the term "server" is often used herein, it will be recognized that this term may also encompass a search service, a search extender service, a Web browser, a cloud server, a set of one or more processes distributed on one or more computers, one or more stand-alone storage devices, a set of one or more other computing or storage devices, a combination of one or more of the above, and the like.

COMPARATIVE EXAMPLES

To demonstrate the accuracy with which protein superimposing program of the current invention superimposes proteins, several homologous proteins were superimposed utilizing both the protein superimposing program of the current invention and the Theseus structural superpositioning program. The Theseus program calculates structural translations and rotations utilizing a derivative-based ML algorithm. To establish the necessary homology of the alpha carbons, Theseus requires a preliminary input sequence alignment. For the Theseus results contained herein, the preliminary sequence alignment was generated utilizing the MUSCLE program.

The root-mean-square deviation (RMSD) spatial distance measurement is utilized to quantitatively assess the quality of a pairwise protein structural superposition. However, calculation of the RMSD requires determining the homology (matching) of amino acid residues. To compare the protein superimposing program of the current invention and Theseus quality assessment scores (e.g., RMSD, etc.) of superimposed proteins, correct methodology requires the derivation of homologous amino acids utilizing the superimposed protein structure. Unfortunately, although Theseus calculates a classical RMSD for pairwise superpositions, the amino acid homology utilized to generate this calculation is derived from the preliminary sequence alignment. Therefore, calculating the most probable sequence alignment derived from superimposed protein structures necessitates use of a structure-dependent sequence alignment (SDSA) program called UniTS (Universal True SDSA). The UniTS program calculates the most probable SDSA utilizing both the spatial distances between homologous atoms and sequential information in structurally nonconserved regions of the superimposed proteins. Utilizing this newly generated SDSA, UniTS calculates improved, structure-based, quality assessment scores for the superimposed proteins.

The protein superimposing program of the current invention does not derive an SDSA, thus preventing the calculation of quantitative assessment scores for its generated structural alignment. Because of this, UniTS was used to supplement these limitations. Therefore, the combination of the protein superimposing program of the current invention and UniTS is capable of calculating a structural alignment, a corresponding sequence alignment, and quality assessment scores for the superimposed proteins. Because UniTS calculates the SDSA and structural quality assessment scores for the superimposed protein derivations of both the protein superimposing program of the current invention and Theseus, the results contained herein are measured utilizing equal (structure-based) methodologies. This eliminates the influence introduced into the results by inconsistent and possibly contrasting measurement methodologies.

Monomeric Pairwise Comparison

To compare the pairwise superimposing capabilities of the protein superimposing program of the current invention and Theseus, four superimposition trials were conducted, where each trial was directed to a protein family consisting of two homologous monomers. Table 1 displays the two PDB designations, the mean sequence length, and the sequence identity characterizing each protein family.

| Protein Family | First Protein PDB | Second Protein PDB | Mean Length | Sequence Identity[b] |
| --- | --- | --- | --- | --- |
| Protein Kinase C | 1BDY[a] | 2ENJ | 127 | 47 |
| Isocitrate Dehydrogenase | 1T09[a] | 1XGV[a] | 422 | 25 |
| Pectate Lyase | 1PLU | 2BSP | 375.5 | 20.3 |
| Polygalacturonase | 1CZF[a] | 1HG8 | 342 | 40.1 | where "[a]" is Chain A of the protein and "[b]" is the sequence identity calculated utilizing the MEGA5 sequence analysis software.

Figure 6:
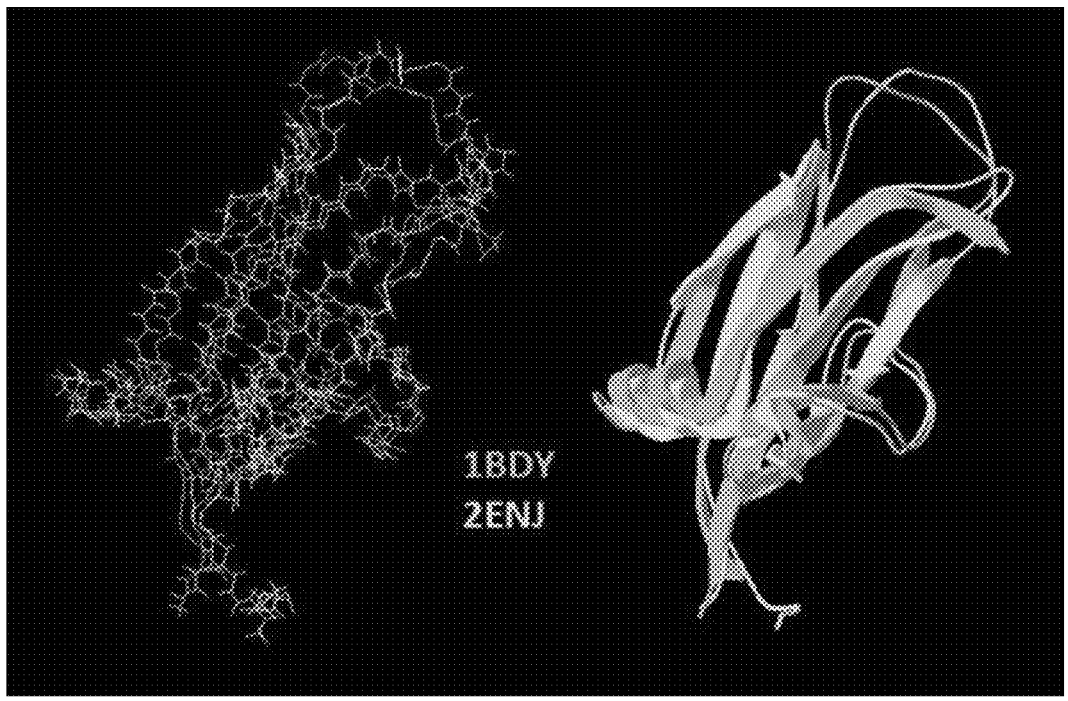
FIGS. 6-9 depict colored illustrations of the structural alignment for four protein families based on the protein superimposing program described herein in accordance with an embodiment of the present invention.
Figure 7:
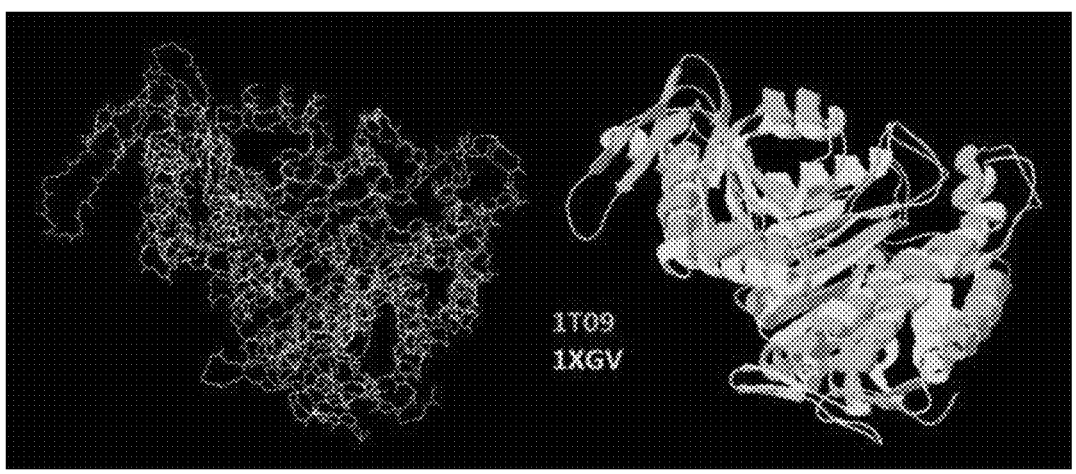
Figure 8:
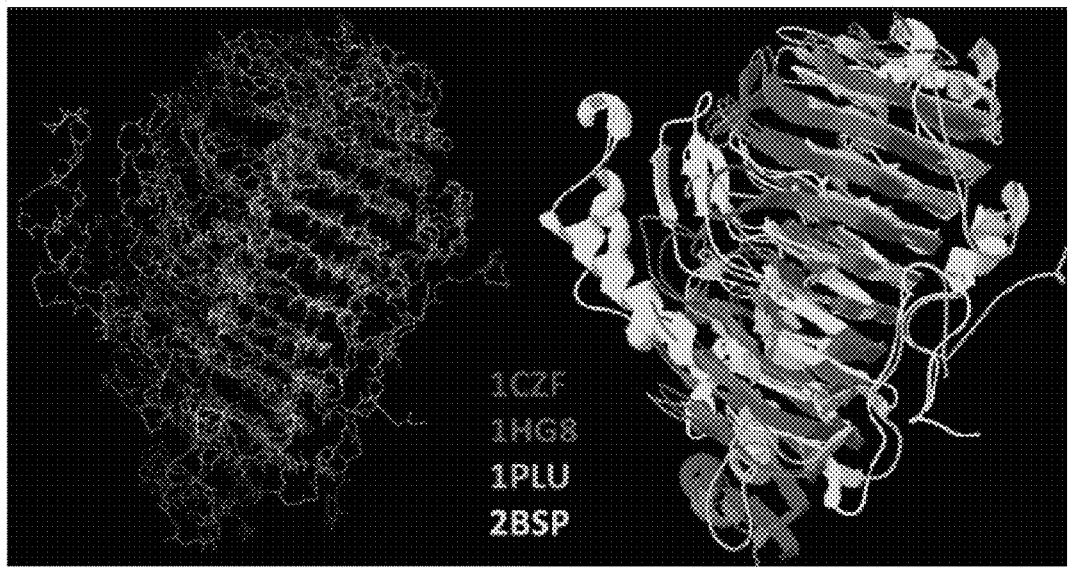
Figure 9:
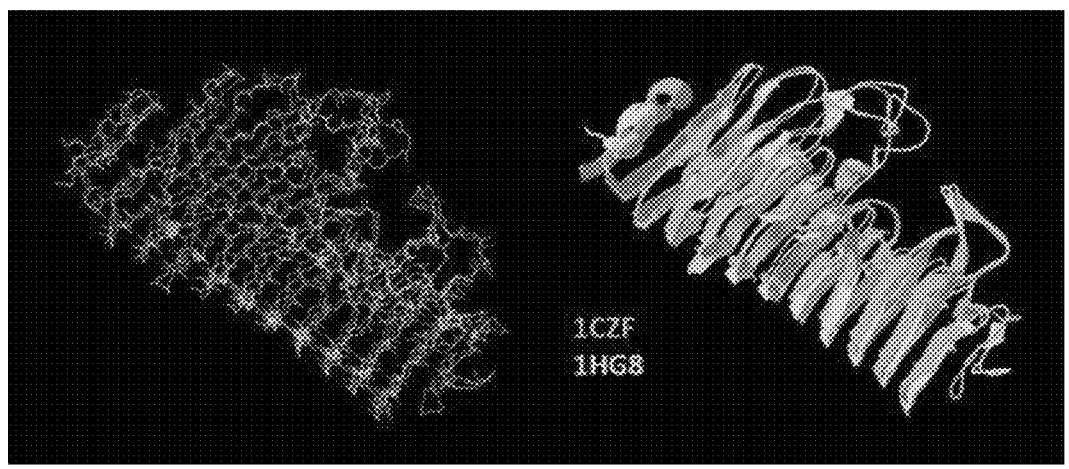

Additionally, FIGS. 6-9 depict images of the structural alignment for each protein family based on the protein superimposing program described herein. More specifically, each of FIGS. 6-9 depicts an atomic image format on the left and a ribbon image format on the right of each pairwise structure alignment generated by the protein superimposing program described herein. FIG. 6 depicts two homologous monomers of the protein kinase C family (e.g., BDY and ENJ), FIG. 7 depicts two homologous monomers of the isocitrate dehydrogenase family (e.g., T09 and SGV), FIG. 8 depicts two homologous monomers of the pectate lyase family (e.g., PLU and BSP), and FIG. 9 depicts two homologous monomers of the polygalacturonase family (e.g., CZF and HG8).

Table 2 elucidates the alpha carbon RMSD values of each superimposed protein family as calculated utilizing both the protein superimposing program and Theseus. As previously stated, Theseus utilizes homologous alpha carbons derived from the MUSCLE sequence alignment to calculate the RMSD. Consequently, the RMSDs derived by Theseus in Table 2 are overinflated while those derived by UniTS for both the protein superimposing program and the Theseus superimpositions are expectedly less.

TABLE 2

RMSDs and statistical significance of protein families.

| Protein Family | SABLE/ UniTS RMSD | Theseus/ Muscle RMSD | Theseus/ UniTS RMSD | UniTS Statistical Significance |
| --- | --- | --- | --- | --- |
| Protein Kinase C | 2.57 Å | 2.69 Å | 2.67 Å | 0.96 |
| Isocitrate Dehydrogenase | 7.21 Å | 15.23 Å | 7.00 Å | 0.97 |
| Pectate Lyase | 7.76 Å | 11.85 Å | 6.19 Å | 0.75 |
| Polygalacturonase | 1.69 Å | 1.99 Å | 1.57 Å | 0.92 |

To statistically compare the protein superimposing program and Theseus pairwise superimpositions, a score of statistical significance was calculated as shown in Table 2. This score determines if the difference between the observed (i.e., calculated by the protein superimposing program and UniTS) and the expected (i.e., calculated by Theseus and UniTS) RMSDs is statistically significant for each protein family by dividing this difference by the expected RMSD. The limited RMSD difference of three pairwise comparisons indicates that the accuracy with which the protein superimposing program superimposes two monomeric proteins is equal to that of Theseus. The two programs, however, exhibited a significant RMSD divergence when superimposing the pectate lyase family. This discrepancy likely results from inconsistent residue matching in the UniTS SDSA rather than the quality of the superimposition. To compare the quality of the SDSA generated utilizing the protein superimposing program to that generated utilizing the Theseus superposition, conventional sequence alignment log-odds scores were calculated for each pectate lyase SDSA. The SDSA generated utilizing the protein superimposing program produced a superior log-odds score of 66.0, while that produced from the Theseus superposition was 58.0. These results indicate that the SDSA generated utilizing the protein superimposing program possesses superior amino acid homology compared to that of the Theseus superposition.

Multisubunit Pairwise Comparison

To elucidate the multisubunit capabilities of the protein superimposing program, the polygalacturonase proteins were superimposed a second time utilizing a homodimeric 1CZF (Chains A and B) and the original monomeric 1HG8. For the Theseus superposition of the polygalacturonase proteins, UniTS calculated a 1.78 angstrom RMSD; furthermore, UniTS calculated a 1.54 angstrom RMSD for the alignment generated from the protein superimposing program. This significant difference between the RMSD measurements demonstrates both the inability of Theseus to accommodate multisubunit superpositions and the proficiency of the protein superimposing program at segregating and differentiating the calculations of independent polypeptide chains.

Two reasons contribute to the inability of Theseus to superposition multisubunit proteins. First, MUSCLE is incapable of differentiating polypeptide chains while generating a sequence alignment. Second, the Theseus algorithm is dependent upon input proteins possessing similar polypeptide sequence lengths; the protein superimposing program, however, is not limited by chain length differentiation. Furthermore, because the protein superimposing program properly differentiates and aligns polypeptide chains, it is limited by neither multiple subunits nor heterogeneous numbers of subunits.

Multiple Alignment Comparison

Figure 10:
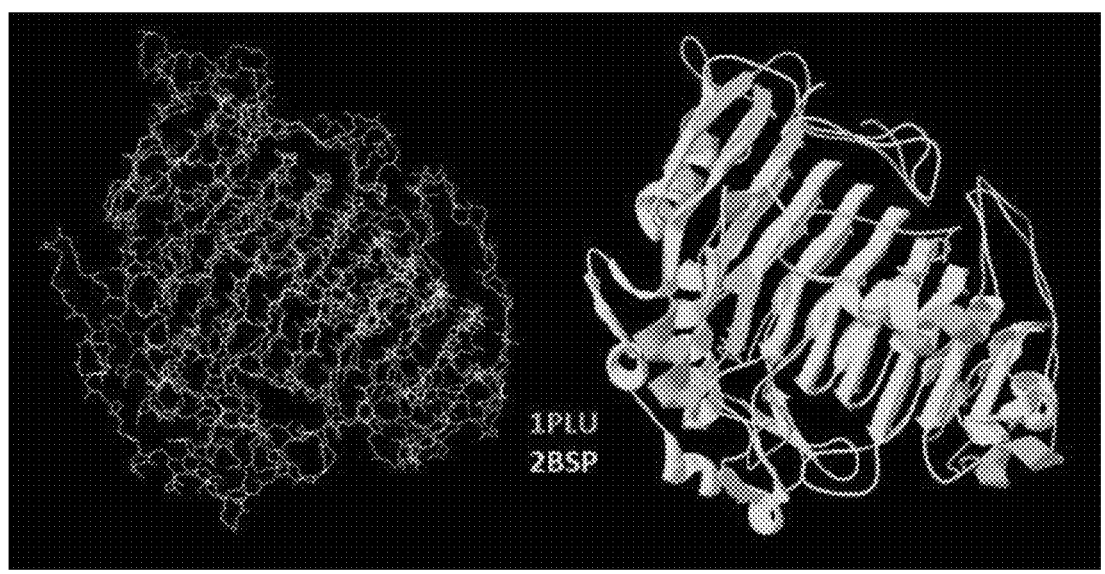
FIG. 10 depicts a colored illustration of a multiple alignment comparison of two protein families based on the protein superimposing program described herein in accordance with an embodiment of the present invention.

To demonstrate the multiple structural alignment capability of the protein superimposing program, four homologous proteins were superimposed utilizing both the protein superimposing program and Theseus. The homologous proteins consisted of two pectate lyase and two polygalacturonase proteins (see Table 1 for specific PDB designations). For each program, the aforementioned proteins were superimposed twice (illustrated in FIG. 10). The first superimposition included the monomeric 1CZF polygalacturonase, while the second incorporated the homodimeric 1CZF.

As with the aforementioned pairwise alignments, UniTS was utilized to quantitatively assess the four quad superimpositions. Superimposing more than two proteins (i.e., a multiple alignment) precludes the calculation of the RMSD for quantitative analysis. Therefore, UniTS performs the quantitative assessment of a multiple protein superposition or structural alignment utilizing the mean standard deviation. Calculation of the mean standard deviation consists of averaging the individual standard deviations of each homologous atom position. As displayed in Table 3, UniTS was utilized to calculate the mean standard deviations of both the protein superimposing program structural alignments and of both Theseus superpositions:

TABLE 3

Mean standard deviations of the quad superimposed proteins

| Program | Single Subunit | Multisubunit |
| --- | --- | --- |
| Protein Superimposing Program | 3.31 Å | 3.41 Å |
| Theseus | 3.36 Å | 4.83 Å |

The results presented herein indicate that the accuracy with which the protein superimposing program superimposes two monomeric proteins is equal to that of the Theseus superpositioning program. Furthermore, for increasingly complex alignments (i.e., increasing the number of input proteins, increasing the number of chains, or by incorporating heterogeneous numbers of chains), the flexibility of the protein superimposing program permits the generation of significantly more accurate superpositions than those generated by Theseus. This versatility and accuracy allows the protein superimposing program to calculate structural alignments with minimal human intervention, reducing the need to curate results and increasing output through automation. Consequently, the protein superimposing program can automate applications such as generating a mean structure from divergent homologous proteins or modeling ligand binding.

What is claimed is:

1. A computerized method carried out by at least one server having at least one processor for utilizing protein structural information to superimpose multiple protein structures, the method comprising:
   selecting a stationary template protein;
   testing, using the at least one processor, a set of input mobile proteins against the template protein by rotating and translating each mobile protein relative to the template protein in a three-dimensional (3D) coordinate space by a predefined distance and predefined angle to generate a set of pseudostates for the each mobile protein;
   scoring the set of pseudostates based on a statistical likelihood of superimposing on the template protein;
   retaining as a subset of the set of pseudostates those pseudostates having scores above a predefined threshold;
   iteratively optimizing and refining the subset of pseudostates for each mobile protein by incrementally decreasing the translational and rotational coordinates until a predefined lower limit is reached to generate successive subsets of pseudostates, wherein low-scoring pseudostates are eliminated after each iteration;
   subsequent to this step, selecting as a new template protein a pseudostate having the least mean center error distance (MCED) as compared to the remaining pseudostates;
   testing the remaining pseudostates against the new template protein with the translational and rotational coordinates being limited as a function of the each pseudostate's respective MCED such that the remaining pseudostates converge towards their lower MCED; and
   retaining as the each mobile protein's final structural alignment, the pseudostate having the highest statistical likelihood of superimposing on the new template protein.

2. The computerized method of claim 1, further comprising generating an output file describing the relative positions in the 3D coordinate space of the each mobile protein's final structural alignment.

3. The computerized method of claim 1, wherein the selected template protein has a larger spatial perimeter than each of the input mobile proteins.

4. The computerized method of claim 3, wherein the translation boundary of the each mobile protein is limited to the spatial perimeter of the selected template protein.

5. The computerized method of claim 1, wherein translation occurs perpendicular to each of the 3D axes in the 3D coordinate space in both a positive and a negative direction.

6. The computerized method of claim 1, wherein rotation occurs unidirectionally around each of the 3D axes in the 3D coordinate space.

7. The computerized method of claim 6, wherein total rotation is equal to one radian.

8. The system of claim 1, wherein prior to scoring the set of pseudostates, the set of pseudostates is filtered to reduce the number of pseudostates in the set of pseudostates.

9. The computerized method of claim 1, wherein superimposing the set of pseudostates on the template protein occurs on an atomic level.

10. The computerized method of claim 1, wherein incrementally decreasing the translational and rotational coordinates of the subset of pseudostates comprises halving the respective coordinates at each iteration.

11. The computerized method of claim 10, wherein the number of pseudostates in each of the successive subsets of pseudostates remains constant.

12. One or more computer-storage media having computer-executable instructions embodied thereon that, when executed by a computing device, performs a method of utilizing protein structural information to superimpose multiple protein structures, the method comprising:
   designating a protein as a first template protein, the first template protein being fixed in position in a three-dimensional (3D) coordinate system;
   receiving a set of mobile proteins as input proteins, wherein for each mobile protein in the set:
     incrementally translating and rotating the mobile protein in the 3D coordinate system relative to the first template protein to generate a first set of pseudostates;

retaining as a second set of pseudostates those pseudostates in the first set of pseudostates that have a probability above a predetermined threshold of superimposing on the first template protein, wherein the superimposing occurs on an atom-by-atom basis;

iteratively translating and rotating each pseudostate in the second set of pseudostates in the 3D coordinate system relative to the first template protein through a bounded translation range and a bounded rotation range to generate successive sets of pseudostates including an interim set of pseudostates after the iterations are complete, wherein after each iteration, retaining as the next set of pseudostates a predefined number of pseudostates having the highest probability of superimposing on the first template protein;

selecting from the interim set of pseudostates for the mobile protein, an interim pseudostate having the highest probability of superimposing on the first template protein for further processing;

identifying from the interim pseudostates selected for further processing a new template protein, wherein the new template protein's interim pseudostate has the least mean center error distance (MCED) as compared to the remaining mobile proteins' interim pseudostates;

for each remaining interim pseudostate, translating and rotating a defined number of times the each interim pseudostate by a defined translation amount and a defined rotation amount relative to the new template protein to produce a final set of pseudostates for the each mobile protein; and from the final set of pseudostates for the each mobile protein, selecting as the each mobile protein's final structural alignment the pseudostate that has the highest probability of superimposing on the new template protein.

13. The media of claim 12, further comprising generating an output file describing the relative positions in the 3D coordinate system of the each mobile protein's final structural alignment.

14. The media of claim 12, wherein the first template protein has a spatial perimeter greater than the each mobile protein in the set of mobile proteins.

15. The media of claim 12, further comprising prior to retaining as the second set of pseudostates those pseudostates in the first set of pseudostates that have a probability above the predetermined threshold of superimposing on the first template protein, filtering the first set of pseudostates by generating a probability of superimposing on the first template protein and discarding those pseudostates that have a probability of superimposing below a second predetermined threshold, wherein the superimposing is based on an every five amino acid basis.

16. The media of claim 12, wherein iteratively translating and rotating the each pseudostate in the second set of pseudostates through the bounded translation and rotation ranges comprises halving the respective coordinates at each iteration until a final translation length and a final rotation angle is reached.

17. The media of claim 16, wherein the defined translation amount and the defined rotation amount by which the each remaining interim pseudostates is translated and rotated relative to the new template protein to produce the final set of pseudostates comprises the final translation length and the final rotation angle.

18. The media of claim 12, wherein the defined number of times by which the each remaining interim pseudostate is translated and rotated relative to the new template protein is a function of the each interim pseudo states' MCED.

19. A computerized system for utilizing protein structural information to superimpose multiple protein structures, the system comprising:
    one or more processors; and
    computer-storage media having computer-executable instructions embodied thereon that, when executed by the one or more processors, cause the one or more processors to:
    identify translational, rotational, and structural alignment pseudostates of a mobile protein;
    generate probabilities for each of the pseudostates and identifies those pseudostates having probabilities above a predefined threshold;
    refine and optimize those pseudostates having probabilities above the predefined threshold; and
    select a pseudostate having the highest probability to be the mobile protein's final structural alignment.

20. The computerized system of claim 19, wherein the one or more processors
    create one or more files describing the relative positions in a three-dimensional coordinate system of the individual atoms of the mobile protein's final pseudostate.

* * * * *